United States Patent
Kalies, Jr.

(10) Patent No.: US 8,560,338 B2
(45) Date of Patent: *Oct. 15, 2013

(54) METHOD FOR COMPETITIVE PRESCRIPTION DRUG AND/OR BIDDING SERVICE PROVIDER SELECTION

(75) Inventor: Ralph F. Kalies, Jr., Pickett, WI (US)

(73) Assignee: TAG, LLC, Pickett, WI (US)

( * ) Notice: Subject to any disclaimer, the term of this patent is extended or adjusted under 35 U.S.C. 154(b) by 739 days.

This patent is subject to a terminal disclaimer.

(21) Appl. No.: 12/281,011

(22) PCT Filed: Mar. 1, 2007

(86) PCT No.: PCT/US2007/063047
§ 371 (c)(1),
(2), (4) Date: Feb. 10, 2009

(87) PCT Pub. No.: WO2007/103714
PCT Pub. Date: Sep. 13, 2007

(65) Prior Publication Data
US 2010/0070298 A1    Mar. 18, 2010

Related U.S. Application Data

(60) Provisional application No. 60/743,387, filed on Mar. 1, 2006.

(51) Int. Cl.
*G06Q 10/00*    (2012.01)

(52) U.S. Cl.
USPC .................. 705/2; 705/3; 705/37; 700/236

(58) Field of Classification Search
USPC ..................... 705/2, 3, 37; 700/236
See application file for complete search history.

(56) References Cited

U.S. PATENT DOCUMENTS

| 5,737,539 A | 4/1998 | Edelson et al. |
| 5,845,255 A | 12/1998 | Mayaud |
| 5,890,129 A | 3/1999 | Spurgeon |

(Continued)

FOREIGN PATENT DOCUMENTS

| EP | 1249786 A2 * | 10/2002 |
| JP | 6168283 A | 6/1996 |

(Continued)

OTHER PUBLICATIONS www.pillbot.com via web.archive.org, Apr. 7, 2003.*

(Continued)

*Primary Examiner* — Dilek B Cobanoglu
(74) *Attorney, Agent, or Firm* — James R Eley; Michael A Forhan; Eley Law Firm Co. LPA

(57) ABSTRACT

Unfilled prescriptions are submitted to a registry comprising pre-qualified pharmacies for a "reverse auction" in which the pharmacies bid for the opportunity to fill the prescription. The pharmacies are allowed to bid based on price and/or offering ancillary services. The auction may also be used to bid on supplying specified pharmaceutical cognitive services. The method may also include obtaining cost comparisons with generic substitutes or similar alternative pharmaceutical products. The system may further comprise automatically requesting a review by the prescriber for a list of similar substitutes or prior-authorization for third party payers. The winner of the reverse auction is selected by the customer.

6 Claims, 9 Drawing Sheets

(56) References Cited

U.S. PATENT DOCUMENTS

| | | | |
|---|---|---|---|
| 5,890,138 | A | 3/1999 | Godin et al. |
| 5,908,788 | A | 6/1999 | Kell |
| 6,014,631 | A | 1/2000 | Teagarden et al. |
| 6,266,652 | B1 | 7/2001 | Godin et al. |
| 6,272,473 | B1 | 8/2001 | Sandholm |
| 6,294,999 | B1 | 9/2001 | Yarin et al. |
| 6,315,720 | B1 | 11/2001 | Williams et al. |
| 6,366,891 | B1 | 4/2002 | Feinberg |
| 6,415,270 | B1 | 7/2002 | Rackson et al. |
| 6,564,192 | B1 | 5/2003 | Kinney, Jr. et al. |
| 6,598,027 | B1 | 7/2003 | Breen, Jr. et al. |
| 6,618,504 | B1 | 9/2003 | Yoshino |
| 6,647,373 | B1 | 11/2003 | Carlton-Foss |
| 6,671,674 | B1 | 12/2003 | Anderson et al. |
| 7,426,476 | B2 * | 9/2008 | Munoz et al. ............ 705/3 |
| 2001/0009005 | A1 * | 7/2001 | Godin et al. ............ 705/37 |
| 2002/0049643 | A1 | 4/2002 | Church |
| 2002/0049771 | A1 | 4/2002 | Nagashima |
| 2002/0052760 | A1 * | 5/2002 | Munoz et al. ............ 705/2 |
| 2002/0059132 | A1 | 5/2002 | Quay et al. |
| 2002/0111829 | A1 | 8/2002 | Robibero |
| 2002/0143434 | A1 * | 10/2002 | Greeven et al. ............ 700/236 |
| 2003/0028482 | A1 | 2/2003 | Burak et al. |
| 2003/0097305 | A1 | 5/2003 | Ogino et al. |
| 2004/0064399 | A1 | 4/2004 | Gologorsky et al. |
| 2004/0073507 | A1 | 4/2004 | Scott et al. |
| 2005/0065821 | A1 | 3/2005 | Kalies |
| 2005/0177392 | A1 * | 8/2005 | Domashnev ............ 705/2 |
| 2006/0178915 | A1 | 8/2006 | Chao |
| 2006/0253366 | A1 * | 11/2006 | Rebibo ............ 705/37 |

FOREIGN PATENT DOCUMENTS

| | | |
|---|---|---|
| JP | 2002007783 A | 1/2002 |
| JP | 2002083170 A | 3/2002 |
| JP | 2002203140 A | 7/2002 |
| JP | 2002251458 A | 9/2002 |
| JP | 2003122830 A | 4/2003 |
| RU | 2105350 C1 | 2/1998 |
| RU | 2144812 C1 | 1/2000 |
| WO | 9737315 A1 | 10/1997 |

OTHER PUBLICATIONS

Google patents search results, May 22, 2013.*
Dialog search results, May 22, 2013.*
http://www.pillbid.com. Apr. 18, 2001 printout.
Harris, Shane "Procurement Bidding Wars" Government Executive May 1, 2001.
FattyTuna.Net "General FAQs" obtained via web.archive.org for the date Mar. 9, 2001.
PillBot.com "FAQ's" obtained via web.archive.org for the date Apr. 7, 2003.
Kreimer, Susan "Generic Versions of Antidepressant Drug Prozac Lower Prices" Houston Chronicle Knight Rider/Tribune Business News Nov. 4, 2004.
ewanted.com for the date Dec. 5, 2000 obtained via web.archive.org/web/20001205030600/http://www.ewanted.com/help/default.cfm.
Frank, Richard, "Prescription Drug Prices: Why do some pay more than others do?" Health Aff (Millwood). Mar.-Apr. 2001;20(2): 115-28.

* cited by examiner

METHOD FOR COMPETITIVE PRESCRIPTION DRUG AND/OR BIDDING SERVICE PROVIDER SELECTION

FIELD OF THE INVENTION

This invention relates to a method for promoting, marketing, distributing, pricing, selling and/or facilitating the delivery of items and/or services obtained through prescriptions. Specifically, the invention relates to a method for reducing the cost of prescription products, services, and/or treatment and increasing the quantity and quality of service provided to the customer through the use of an optional competitive-bid bidding service provider selection process.

BACKGROUND OF THE INVENTION

Spending on prescription drugs continues to be one of the fastest-growing healthcare costs facing customers. Factors that have driven the increases in prescription drug spending include increased use of disease-preventative and quality-of-life enhancing drugs by patients, direct marketing to patients by pharmaceutical companies, usage changes to newer, higher-cost drugs, and price increases by manufacturers and the lack of prescriber and customer information and participation in pharmacoeconomic discussions and choice. A particular problem with prescription drug costs is that many patients who lack prescription drug coverage often pay more for prescriptions than those who do have coverage. This is usually due to "cost shifting" by pharmacies, who attempt to collect larger profit margins from patients with limited buying power and information to compensate for the reduced profits available from insured patients having prescription plans with pre-negotiated price schedules. The result is that uninsured patients, who have little or no market leverage as individuals, pay higher prices for prescriptions than other payers in the marketplace, such as third party payers, insurance companies, the government and the like.

In order to assist those individuals who lack prescription drug coverage, discount drug card programs have been offered by organizations wherein subscribers to the programs receive monetary discounts from participating pharmacies. However, since the discount drug card programs require that the patient pay 100% of the price of the prescription at the time they receive the medication, and since the pharmacist may not be required to adjudicate benefits or discounts through a third party, there is no assurance that the patient will receive the correct discounted price and the patient advocacy that the participating pharmacy had originally contracted to provide under the terms of the discount drug card program.

Third party payment programs, on the other hand, have used many tools to control drug costs; they decreased treatment options, cut pharmacy services, received perverse incentives from pharmaceutical manufacturers, increased co-pays to decrease costs and/or access to some drug therapies, and limited access to providers.

Many patients are unable to purchase needed medication because it is either too expensive or limited by their health insurance plan. Such patients are considered to be "undertreated." Undertreated patients are prone to treatment failures, often must be hospitalized at a greater expense to the healthcare system, and frequently suffer increased morbidity and mortality.

The current system is replete with perverse methods to shift the cost of drug therapy to the customer by means of various incentives for the prescribers, dispensers, consultants, PBM's, HMO's, insurance companies, and others. These perverse incentives act to increase patients' cost of drug therapy or prevent patients from receiving desired products and/or pharmacy services, satisfying profitability motives of the above-listed parties at the expense of the customer. There is a need for tools that allow customers to obtain prescription drugs and services and to consistently provide drug price discounts to customers and increases the availability of desired pharmacy services while holding down the total cost of health care.

SUMMARY OF THE INVENTION

The present invention is a tool which allows customers to obtain prescription drugs and services and provides these customers with a means to reduce the cost of prescription medications and increase their access to desired pharmacy services and also overcomes the shortcomings of using discount cards, PBMs, HMOs, health insurance plans, government plans, and the like.

In one embodiment, the invention is a method for facilitating the delivery of prescription products or services, the method comprising the steps of: providing unfilled prescription information and patient information from a customer to a participating bidding service provider, wherein the prescription was provided to the customer by a prescriber; transferring the unfilled prescription information from the bidding service provider to a registry of pre-qualified prescription fulfillment providers; conducting a reverse auction on a computer system in which the pre-qualified prescription fulfillment providers respond with interactive and iterative bids to fill the unfilled prescription; providing the customer with the details of the lowest bid of each responding prescription fulfillment provider that made at least one bid to fill the prescription; selecting the winning bid by the customer; and providing the customer with a reservation, wherein the reservation comprises at least one coupon for an item other than the prescribed product or service.

In another embodiment, the invention is a method for facilitating the delivery of prescription products or services, the method comprising the steps of: providing unfilled prescription information and patient information from a customer to a participating bidding service provider, wherein the prescription was provided by a prescriber; transferring the unfilled prescription information from the bidding service provider to a registry of pre-qualified prescription fulfillment providers; conducting a reverse auction on a computer system in which the pre-qualified prescription fulfillment providers respond with interactive and iterative bids to fill the unfilled prescription; providing the customer with the details of the lowest bid of each responding prescription fulfillment provider that made at least one bid to fill the prescription; and, selecting the winning bid by the customer, wherein the pharmacy provides the prescribed product from a central prefill location.

In a further embodiment, the invention is a method for facilitating the delivery of prescription products or services, the method comprising the steps of: providing unfilled prescription information and patient information from a customer to a participating bidding service provider, wherein the prescription was provided by a prescriber; transferring the unfilled prescription information from the bidding service provider to a registry of pre-qualified prescription fulfillment providers; conducting a reverse auction on a computer system in which the pre-qualified prescription fulfillment providers respond with interactive and iterative bids to fill the unfilled prescription; providing the customer with the details of the lowest bid of each responding prescription fulfillment provider that made at least one bid to fill the prescription; and, selecting the winning bid by the customer, wherein the prescription is sent electronically to the fulfillment provider having the winning bid.

Another embodiment of the invention is a method for facilitating the delivery of prescription products or services, the method comprising the steps of: providing unfilled prescription information and patient information from a customer to a participating bidding service provider, wherein the prescription was provided by a prescriber; transferring the unfilled prescription information from the bidding service provider to a registry of pre-qualified prescription fulfillment providers; conducting a reverse auction on a computer system in which the pre-qualified prescription fulfillment providers respond with interactive and iterative bids to fill the unfilled prescription; providing the customer with the details of the lowest bid of each responding prescription fulfillment provider that made at least one bid to fill the prescription; and, selecting the winning bid by the customer, wherein the fulfillment provider with the winning bid does not use the Internet to access the bidding service provider and reservation and transaction information is transmitted between the bidding service provider and the fulfillment provider with the winning bid through a data interchange system.

A further embodiment of the invention is a method for facilitating the delivery of prescription products or services, the method comprising the steps of: providing unfilled prescription information and patient information from a customer to a participating bidding service provider, wherein the prescription was provided to the customer by a prescriber; electronically performing a similar product price comparison to identify a list of products potentially similar to the prescribed drug along with relative costs for such identified similar products; providing the customer with the results of the similar product price comparison; selecting the product from the similar product price comparison by the customer, with the approval of the prescriber; providing the customer with a list of fulfillment providers based on criteria set by the customer; selecting a fulfillment provider by the customer to fill the prescription; transferring the unfilled prescription information from the bidding service provider to the selected fulfillment provider; providing the customer with a reservation, wherein the reservation comprises at least one coupon for an item other than the prescribed product or service.

Yet another embodiment of the invention is a method for facilitating the delivery of prescription products or services, the method comprising the steps of: providing unfilled prescription information and patient information from a customer to a participating bidding service provider, wherein the prescription was provided to the customer by a prescriber; electronically performing a similar product price comparison to identify a list of products potentially similar to the prescribed drug along with relative costs for such identified similar products; providing the customer with the results of the similar product price comparison; selecting the product from the similar product price comparison by the customer, with the approval of the prescriber; providing the customer with a list of fulfillment providers based on criteria set by the customer; selecting a fulfillment provider by the customer to fill the prescription; transferring the unfilled prescription information from the bidding service provider to the selected fulfillment provider; and providing the customer with a reservation, wherein the reservation comprises at least one coupon for an item other than the prescribed product or service, wherein the pharmacy provides the prescribed product from a central prefill location.

BRIEF DESCRIPTION OF THE DRAWINGS

Further features of the present invention will become apparent to those skilled in the art to which the present invention relates from reading the following specification with reference to the accompanying drawings.

DESCRIPTION OF THE PREFERRED EMBODIMENTS

Figure 1A:
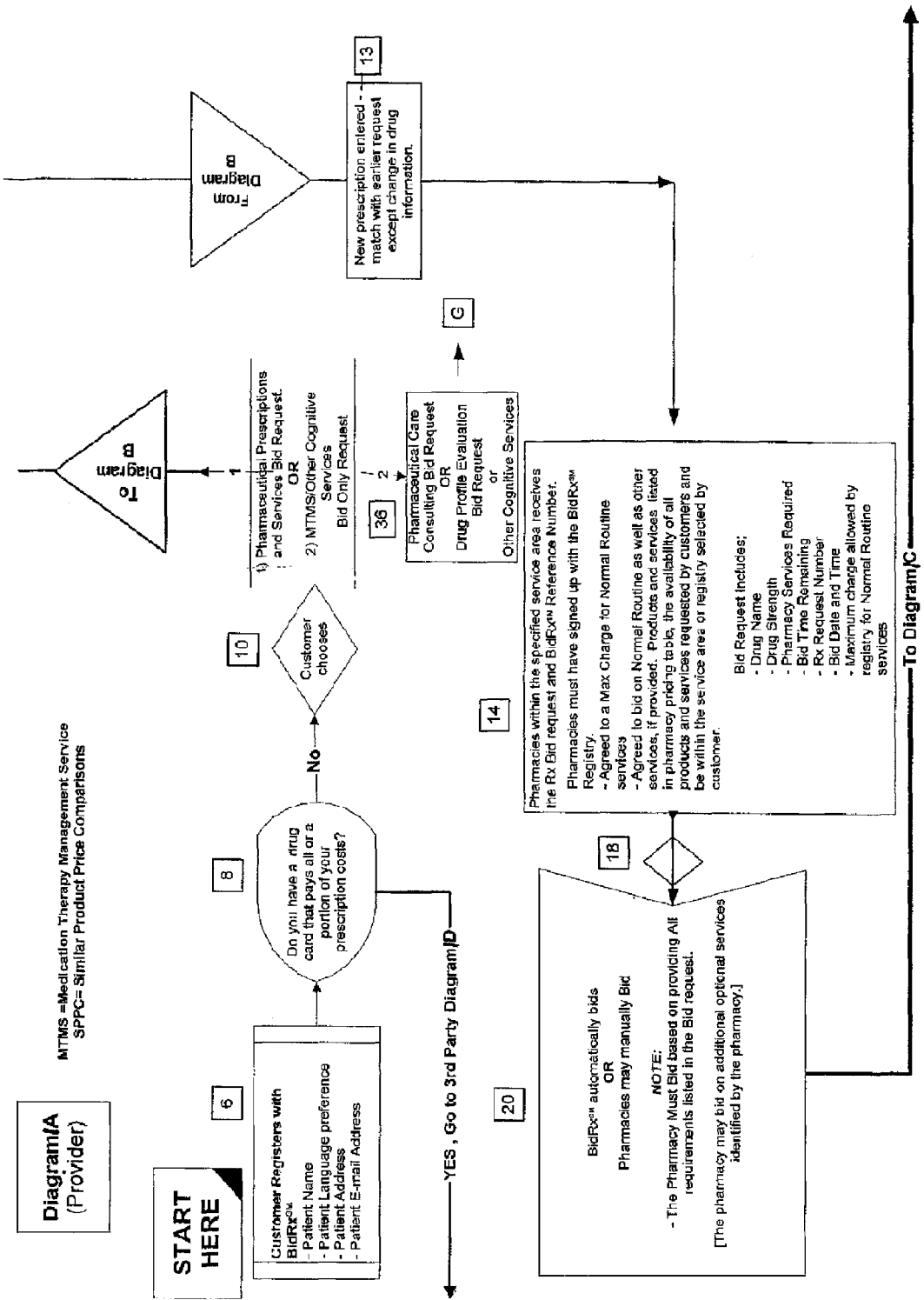
FIG. 1 A-G is a flow diagram of a method for competitive prescription drug and/or bidding service provider selection.

As used herein, the term "prescription" refers to any product or service delivered in a health care setting, such as an order by an authorized person for the preparation and/or administration of a medicine, medical device, any other healthcare related services, or other treatment. Authorization to give a prescription is typically controlled by government or professional associations. Authorized persons may include, as non-limiting examples, physicians, opticians/optometrists, dentists, surgeons, veterinarians, etc. Other treatments can include, inter alia, surgery, physical therapy, psychiatric therapy, corrective lenses, chiropractic treatment, and/or diagnostic testing. The prescription is filled by the appropriate pre-qualified prescription providers (i.e., dispensers of products or services, e.g., pharmacies, physicians, optical shops, dentists, surgeons, hospitals, etc.). For the sake of clarity, the following description will focus on the embodiment where the prescription is for medication and the pre-qualified prescription providers are pharmacies. One skilled in the art will recognize that the invention described herein may be modified as warranted by the idiosyncrasies of other embodiments of prescriptions and/or pre-qualified prescription providers.

A customer is a person who buys the medical or health related goods or services. A consumer is a being who uses or consumes the medical or health related goods or services. A patient is a being receiving medical attention, care, or treatment. A customer is not necessarily a consumer or patient and vice versa (e.g., a parent buying medication for a minor child; an owner obtaining medical treatment for a pet). The payer is the entity that pays for the medical or health related goods or services. The payer may be the customer or a third party, such as a benefit plan or insurance. For illustration purposes only, the following description focuses on the case where the customer is also the patient/customer and these terms will therefore be used interchangeably in this specification.

According to the present invention, a method is disclosed whereby a customer, such as a patient holding a prescription for medication, provides prescription and patient information to a participating bidding service provider/administrator (also called "BidRx$^{SM}$" herein). The prescription may be written, electronic, faxed, verbal or telephonic. The prescription, if in physical form (e.g., written), remains with the patient or the patient's agent. The bidding service provider supplies the unfilled prescription information (minus patient identifying information) to a registry of pharmacies that have been previously qualified by the bidding service provider to participate in a bidding process to fill that specific customer's unfilled prescription within a defined service area and/or selected or defined registry and/or via mail order. The prescription information from the customer is preferably transferred electronically, such as by means of an intranet or the Internet although other means of transfers such as fax, written, etc. are possible.

Third party payers also load in information on the benefit plan features, such as maximum payments, rebates, coordination of benefit requirements, membership lists, etc.

Registry pharmacies which respond to the invitation to bid (i.e., in registry, service area, provide product and service requested, etc.) (called "responding pharmacies" herein), each interact iteratively with the bidding service provider, attempting to provide a better fit for the patient/customer than competing pharmacies in the registry with a lower price and/or additional ancillary services in a "reverse auction." Immediately and continuously the customer is provided information pertaining to the bids of the responding pharmacies until either the customer selects a bid or the pre-selected bidding period ends (at which time, the customer can select their preferred bid or decline all bids).

The customer selects from the responding pharmacies based on idiosyncratic criteria such as: preferred pharmacies (all information related to the pharmacy is included in the bid as well as an optional pharmacy web site link), cost, ancillary services offered, proximity of the responding pharmacies to the customer, and so on. The selected pharmacies are then notified of the customer's selection via the bidding service provider. The customer and the successful responding pharmacy are then provided with a reservation number (the customer is also provided with a key code or key number) and the patient's proper information corresponding to the bid-upon specifications and terms of the prescription transaction, allowing the customer to begin the process of presenting the prescription for the pharmacy to fill and the pharmacy to contact the patient to increase compliance.

A first alternate or additional embodiment of the present invention includes an optional module in which the bidding service provider may, typically for a fee, provide a list of similar product price comparison (SPPC) and provide a list of potential alternative drugs that are similar but may have relatively lower cost. The bidding service provider may also be authorized by the customer to send the customer's prescribing physician the SPPC list for the prescriber's appropriate review, and, if necessary, prior authorization, patient interactions, discussion, and action. The fee charged by the bidding service provider may be a flat fee, or alternatively may be a percentage of the savings being provided to whomever is paying for the prescription. A fee may also be charged to transfer the list to the prescriber.

A second alternate or additional embodiment includes an optional module in which pharmaceutical manufacturers may participate in the bidding process, either directly or indirectly. Pharmaceutical manufacturers may also provide incentives to patients (i.e., a new form of direct-to-customer advertising or coupon) in hopes of generating positive shifts in the market share for products provided by the manufacturers and to further decrease the cost of medication to the customer while allowing diffusion of innovation. Preferably all costs, funds, and coupons are handled electronically. This system also offers direct to consumer (DTC) advertising and/or a web link for product information at the time of purchase and product selection.

A third alternate or additional embodiment of the present invention includes an optional module in which the bidding service provider may have a plurality of tools for the third party to directly set up service plans, co-pay and deductibles for all prescriptions and services. For example, the bidding service provider tool may offer the set up of a basic plan or more comprehensive packages having additional benefits or restrictions offered for a fee basis. Additional benefits may include a profile review of the BidRx$^{SM}$ users' medication, checking for such potential problems as under- or over-medication and potential drug interactions. Subscribers may also be offered ancillary service plans and incentive "points" for prescriptions that may be accumulated for discounts and further benefits. The system may optionally allow for customer feedback and professional pharmacy affiliation feedback.

FIG. 1A-F is a flow diagram of a preferred embodiment method for competitive prescription drug provider selection. The method shown in FIG. 1 demonstrates all of the above optional modules, also.

At Step 6 a customer, such as a patient receiving a prescription, registers with a bidding service provider (also labeled herein as "BidRx$^{SM}$"). The bid request may be transmitted to the participating bidding service provider via an electronic network, such as an intranet or the Internet. Alternatively, the order may be placed by conventional means, such as in-person, by telephone, mail order or facsimile. At Step 6, customers register for the service by providing the following identification and communication information, for example: (1) Customer Name; (2) Customer Language preference; (3) Customer Address; and (4) Customer Email Address.

After Step 6, the customer may initiate a Pharmaceutical Prescriptions and Services Bid Request. At Step 8, the customer will be asked, "Do you have a drug card that pays for all or a portion of your prescription costs?" If "NO" continue on, if "YES" the customer will be directed to the third party/Insurance Module (FIG. 1D).

At Step 10, the customer will have a choice of whether to select; 1) Pharmaceutical Prescriptions and Services Bid Request; or, 2) Medication Therapy Management Service (MTMS)/Pharmaceutical Cognitive Services Only Bid Request. If the customer selects 1), the process continues at FIG. 1B. If the customer selects 2), the process continues at FIG. 1G.

Steps 6-10 may automatically download from the registration information.

Figure 1B:
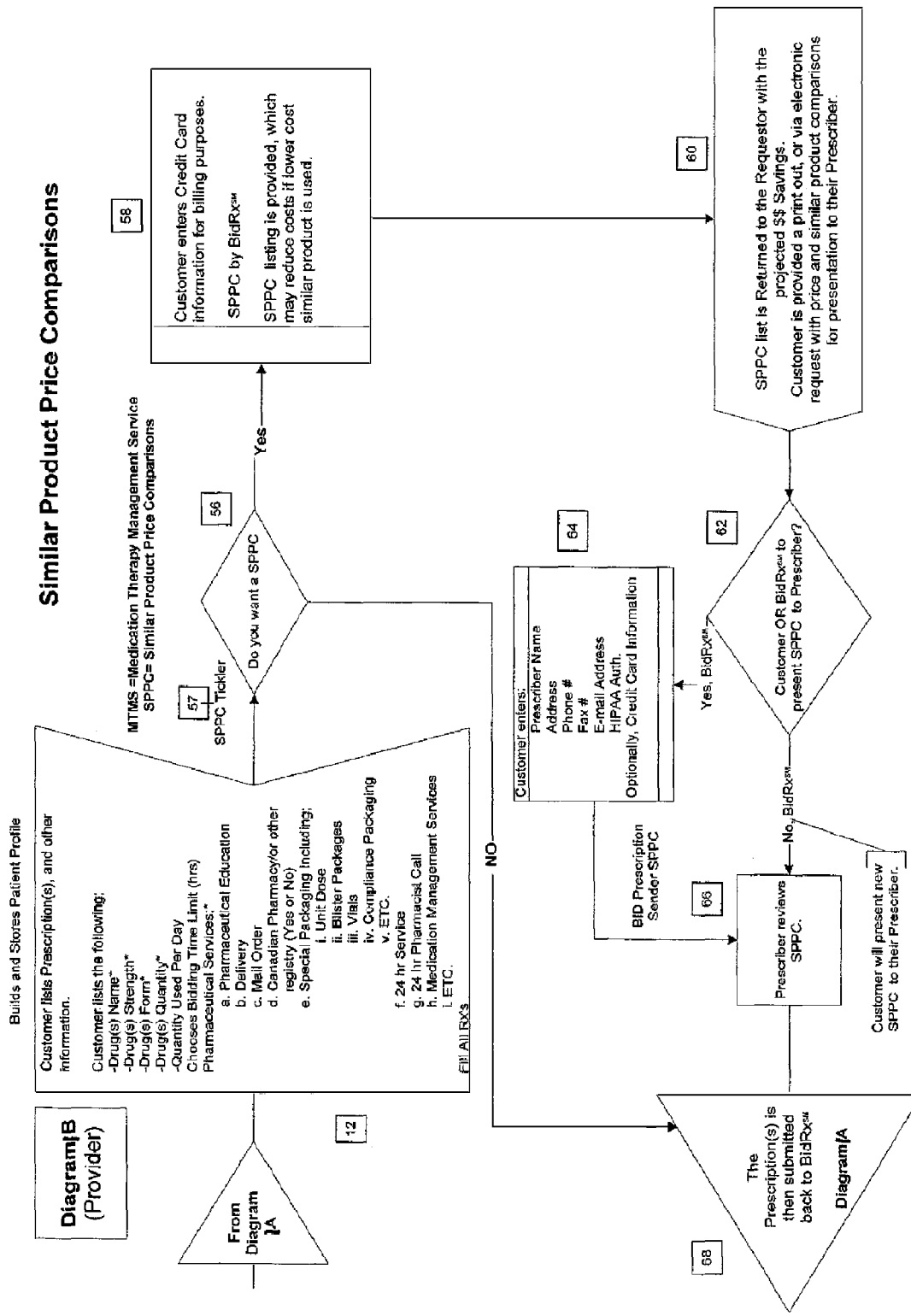

Referring to FIG. 1B, at Step 12 the customer may add to his/her profile and/or provide the bidding service provider with information pertaining to the bid request, may include but not limited to patient name, patient language preference, patient address, patient Email (address may already be there from registration). The customer or proxy or advocate also adds the prescription information, such as, prescription name, drug strength, the form of the drug (i.e., tablets, capsules, gelcaps, etc.), prescription quantity, amount taken per day, potentially directions for use, any ancillary pharmacy services desired, and a bidding time limit (normally in hours). Step 12 may be made more efficient by the bidding service provider, by storing at least a portion of the customer-specific information, such as name, preferences, and addresses, in a physical file or an electronic database and then later recalling the information when another prescription is presented by the customer. Additionally, information pertaining to the drug (name, strength, etc.) and/or the pharmaceutical services are preferably selected by the customer from drop down menus or a similar process in order to reduce mistakes.

If a separate fee is charged for the Similar Product Price Comparison (SPPC), the customer is then asked at Step 56 if they would like an SPPC prior to submitting their bid for product and services. If the SPPC is free, the SPPC may be automatically generated. A tickler message 57 can be used to inform the customer of the magnitude of potential savings. In the SPPC process, 58, the bidding service provider provides a list of drugs at similar potency that compares the drug products the customer has listed for bid. In many cases, the SPPC list may indicate the availability of potentially lower cost similar products. Some examples of the list at Step 60 is shown in Table 1:

TABLE 1

Example SPPC List

| Drug | Cost | third party Coupon | Co-Pay | Customer Coupon | You Pay | PA |
|---|---|---|---|---|---|---|
| A | $140.00 | 0 | $140.00 | $20.00 | $120.00 | Yes |
| B | $140.00 | $25.00 | $ 20.00 | $10.00 | $ 10.00 | Yes |
| C | $100.00 | 0 | $ 20.00 | 0 | $ 20.00 | No |
| D | $100.00 | $20.00 | $ 10.00 | 0 | $ 10.00 | No |
| E | $ 80.00 | $20.00 | $ 10.00 | $20.00 | 0 | No |

Table 1 has columns for third party coupons and customer coupons. Coupons are discounts from the manufacturer/supplier (also called "PhRMA" herein) of the drugs that reduce the cost of the prescription to third party payers and/or the customer. The customer coupons act as an incentive for the customer to choose the manufacturer's product by reducing the amount that the customer must pay. Likewise, third party coupons decrease the cost to the third party payer, who may then pass some of the savings on to the customer either by reducing the co-pay and/or not requiring a prior authorization (PA) in order to urge the customer proxy/advocate to choose the manufacturer's product (compare Example Drugs A-D in terms of the co-pay amounts and PA requirements in relation to the cost to the third party). Typically, the cost to the customer will not be allowed to be less than zero (Example Drug E). PhRMA can also provide web links so that the customer can obtain more information on the drugs. Additionally, PhRMA could have direct-to-customer advertising linked to the SPPC list. Other consumer links may be made available.

Other variations of these coupons are also included within the scope of this invention. For example, a PhRMA entity may provide a sample coupon that would pay the entire product cost. Such a sample coupon would allow a prescriber to give a trial sample to the consumer without having to dispense the drugs themselves. Another example is a sponsored pharmacy coupon which is intended to allow manufacturers of generic products to promote the use of their products. Typically, the bidding service provider will lump one or more generic products into a single category for the SPPC. The manufacturer can offer a coupon which pays only if their own product is dispensed thereby encouraging pharmacies and providers to dispense the promoted products. In one embodiment, the coupon value will be paid by the pharmacy/provider if that entity does not dispense the promoted products. Still another type of coupon would be an SPPC fee coupon. An SPPC fee coupon would allow a PhRMA or other entity to provide competitive product information to the consumer. If an identified product is listed as an alternative in an SPPC report, then the PhRMA or entity will pay for the SPPC report in order to show the consumer their competitive products. Frequently, a link will be provided to allow the consumer to view the competitive product information thereby providing an opportunity for the PhRMA entity to compete on product attributes rather than just on costs.

The availability of coupons can be restricted or targeted in various ways. For example, the PhRMA supplier can have coupons that will be applied if the originally bid product is supplied by a competitor, but will not be applied if the originally bid product is the manufacturer's own product or if product is already the lowest cost. Additionally, coupons could be restricted to the type of payer (private payer only, third party member only, etc.) or by state, region, zip code, pharmacy chain, doctor group, etc.

In one embodiment, the reservation can include other direct-to-consumer coupons. Preferably, these coupons would be targeted to the consumer or other criteria in various ways, such as tied to the prescribed drug, tied to the consumer's demographics, or tied to the individual pharmacy. Examples of the first tie-in might include a coupon for diapers tied to a prescription for an ointment for controlling diaper rash. Likewise, the demographic information provided by the consumer might be used to target coupons for feminine products to women consumers. Pharmacy-related coupons could include coupons for store brands or for specials being run by the pharmacy or, for instance, if the pharmacy was a full-scale store such as a Sam's Club, the coupon could be for other merchandise such as bicycles or general advertising.

Of course, a change from the customer's current medication to a lower cost product must be approved by the prescriber. Additionally, a different medication may necessitate a prior authorization (PA). At Step 62, the customer is given the option to either directly contact the prescriber with the SPPC list for potential change to a lower cost product or else authorize the bidding service provider to send the SPPC list to the prescriber for the customer.

If the customer opts at Step 62 for bidding service provider to send the SPPC list to the prescriber, then the customer provides the following information at Step 64, then the information is automatically transferred by the bidding service provider.

Prescriber Name
Address
Phone Number
Fax Number
Email address if available
HIPAA Authorization (Statement Check Box)
Credit Card Information In Step 66, the prescriber reviews the SPPC list, whether presented by the customer or the bidding service provider. The prescription, reflecting the prescriber's approval/disapproval of the SPPC listed options, is then resubmitted to the bidding system prior at Step 14 (FIG. 1A). If necessary, a new prescription is entered at Step 13.

The prescriber can act as a proxy for the customer. In this embodiment, the prescriber can see the customer's cost at the time of making the prescription. If prior authorization is needed, the prescriber can provide the authorization online, which may influence the cost to the customers (this is because under the terms of some health care plans some drugs have lower copays, or costs (i.e., "u-pay") if a doctor certifies that lower cost drugs are not effective for the patient).

If the customer selects "NO" for the SPPC at Step 56 (FIG. 1B), then the bidding service provider system determines the customer's geographic service area based on a chosen mile radius, and requested services and sends the appropriate customer information for bid to the appropriate pharmacies in the registry database as shown at Step 14. The Customer Service Area is defined as all pharmacies enrolled in the bidding service provider registry database that are in the service area defined by the customer within a given distance, e.g., a 10-mile radius from the customer, by geomapping method or the customer zip code plus all adjoining zip codes or are Mail Order pharmacies (as designated by the National Council for Prescription Drug Providers (NCPDP) indicator or Registry database field in the Mail Order registry) if mail order selected. The Canadian pharmacy registry or other registry is included if selected by the customer. The pharmacies chosen will be within the geographic area selected by the customer, or may be a mail order pharmacy if that was selected by the customer. The customer may also be asked if Canadian pharmacies or other registry country/type of pharmacies can bid on the prescription and/or service items. If "YES", the bid information is sent to any Canadian pharmacies and other registry country/type of pharmacies selected in the bidding service provider's Canadian provider registry and other registry country/type.

At Step 14, pharmacies that have joined the bidding service provider registry through a qualification process and are within the customer's service area (or are able to provide mail-order service if selected) will receive a notification of the prescription bid request from the bidding service provider and an invitation to bid. Such notification is preferably via electronic means, for example an intranet or the Internet (although other means of notification could be used). The qualification process may include criteria such as agreeing to maximum charges for normal and routine products and services; agreeing to bid on normal and routine products and services per a registry contract as well as bidding on other requested services for the price listed on the pharmacies pricing table charge if service(s) available as well as adding other services not requested to the bid including, but not limited to, pharmaceutical education, various delivery methods (such as mail order, walk-in and institutional), providing desired prescription packaging (such as unit dosing and vials), 24 hour service, 24 hour pharmacist on-call; and agreeing to fill all prescriptions presented for a particular reservation according to the reservation at no charge and honor all other conditions of the registry agreement. Preferably, the bidding system provider defines minimum requirements that must be met for a service to be claimed by a pharmacy (e.g., 24 hour service means that a pharmacist must be on-site 24 hours a day, every day).

Figure 2:
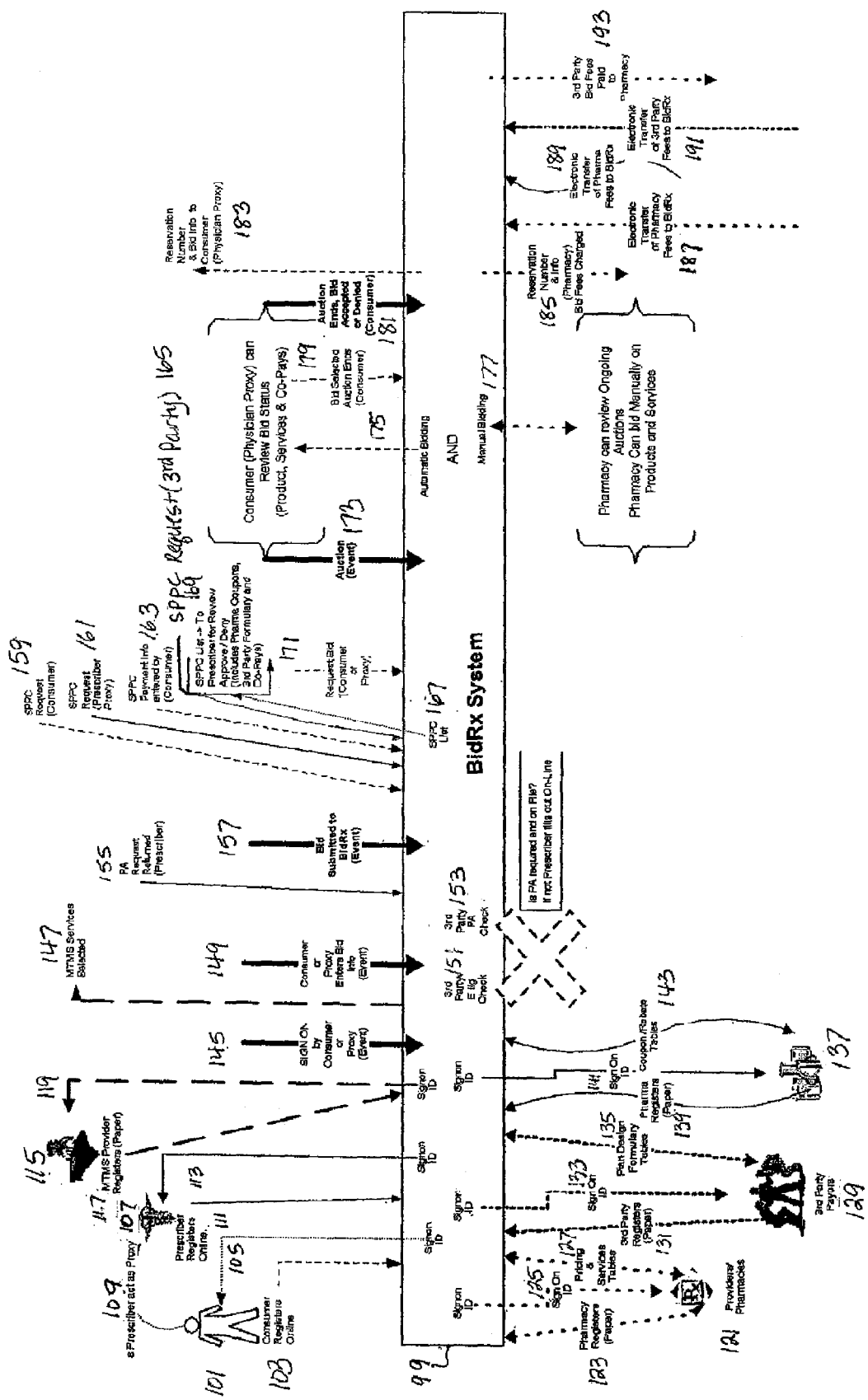
FIG. 2 is a timeline of a representative bidding system.
Figure 3:
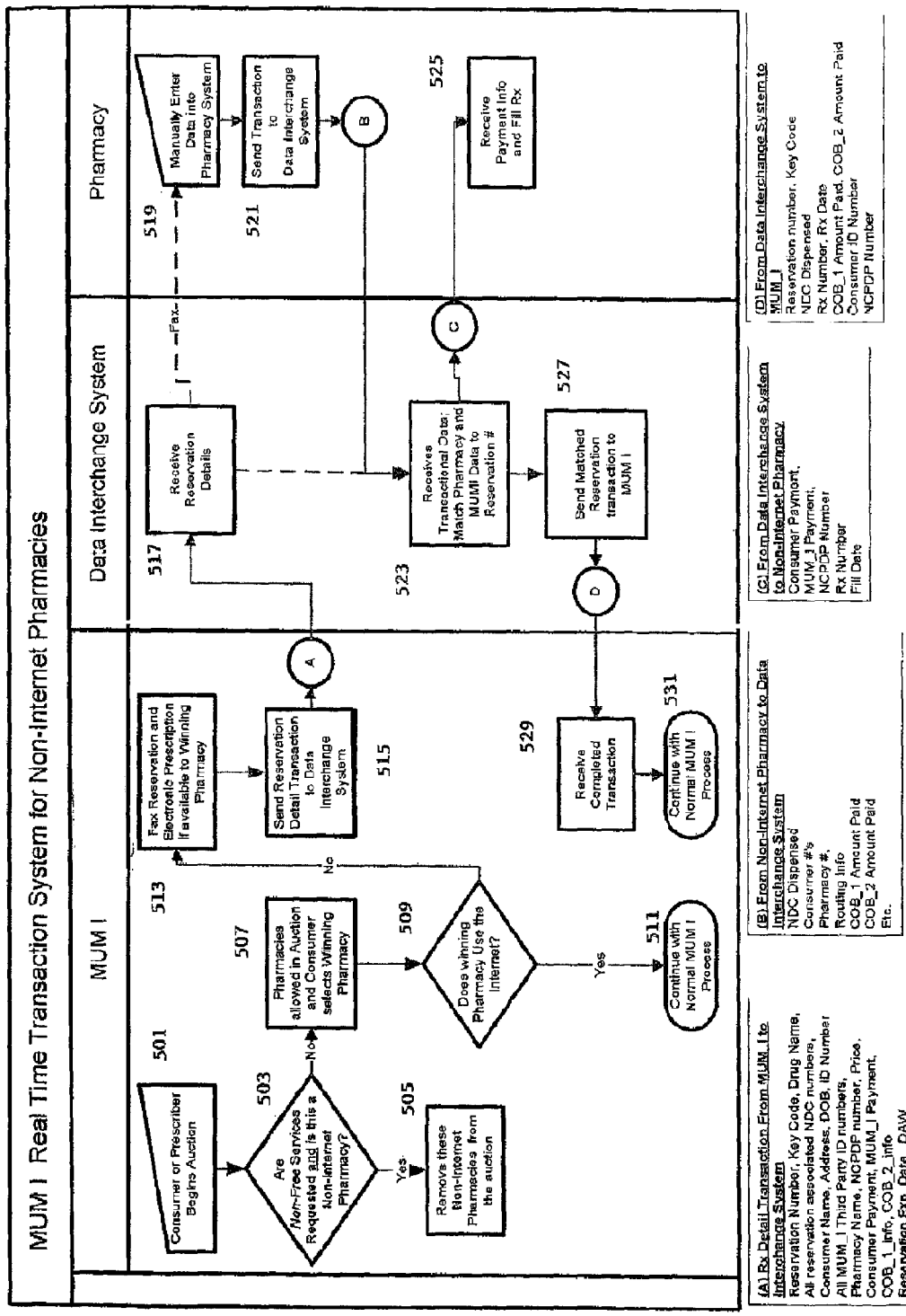
FIG. 3 is a flow diagram of a subsystem for non-Internet pharmacies.

FIG. 3 shows a flow chart of a subsystem for handling real time transactions for non-Internet pharmacies. In Step 501, the consumer or prescriber begins the auction as previously described unless a manual process used for collection. The system reviews the auction request in Step 503 to determine if non-free services are requested and if the potential bidding pharmacies are non-Internet pharmacies. If both conditions are true, then in Step 505 the non-Internet pharmacies are removed from the auction. If at least one of the conditions in Step 503 is not true, then the pharmacy is allowed into the auction in Step 507 and the consumer selects the winning pharmacy as previously described. In Step 509, the system determines whether the winning pharmacy uses the Internet. If the pharmacy uses the Internet, then in Step 511 the normal procedure is used as previously described. If the winning pharmacy does not use the Internet, then in Step 513 the reservation and an electronic prescription, if available, is transmitted by facsimile or electronically to the winning pharmacy. In Step 515, the reservation and details of the transaction are sent to a data interchange system. The data interchange system is typically an electronic medium, such as a server, but could also be done manually. The transaction details typically include information such as reservation number, a key code, the drug name, all reservations, associated National Drug Code (NDC) numbers, consumer name address and other personal information, third party identification numbers, pharmacy name and number, price, consumer payment, system payment, and reservation expiration date. In Step 517, the data interchange system receives the reservation details. The reservation details are forwarded to the pharmacy by facsimile other methods or e-prescriptions in Step 519. The pharmacy then manually enters the data into the pharmacy's system. The pharmacy in Step 521 then sends transaction details back to the data interchange system. The data sent back from the pharmacy typically includes the information and formatting required by NCPDP, such as NDC dispensed information, consumer numbers, pharmacy numbers, prescription information, coordination of benefits information, etc. Both the reservation details received in Step 517 and the transaction details sent in Step 521 are received by the data interchange system in Step 523. The system then matches the pharmacy and system data to the reservation number. The data interchange system then sends information such as consumer payment, system payment, NCPDP number, prescription number and fill date to the pharmacy in Step 525. The pharmacy receives the payment information and fills the prescription. In Step 527, the matched reservation information from Step 523 is transmitted back to the bidding system. The information exchanged from the data interchange system typically includes the reservation number, key code, NDC dispensed, prescription number, prescription date, coordination of the benefits information, consumer identification number, and the NCPDP number. In Step 529, the bidding system receives the completed transaction information and in Step 531 continues with the normal bidding system process as described elsewhere (e.g., Step 187 of FIG. 2).

The pharmacy responds to the bidding request by the pharmacy placing a bid (manually or automatically), which must conform to all requirements requested by the customer and contained in the bid request at Step 12. The responding pharmacy may also include additional optional services in the bid. Each responding pharmacy submits its bid to the bidding service provider at Step 20. The bids are preferably transmitted from the responding pharmacy to the bidding service provider electronically, such as by means of an intranet or the Internet, though alternate forms of communication such as telephone, facsimile and mail, although not preferred, may be used.

In an alternate embodiment, pharmacies may be given the option to bid or not. Generally, bidding option 18 will not be available in order to maximize pharmacy participation 18.

Figure 1C:
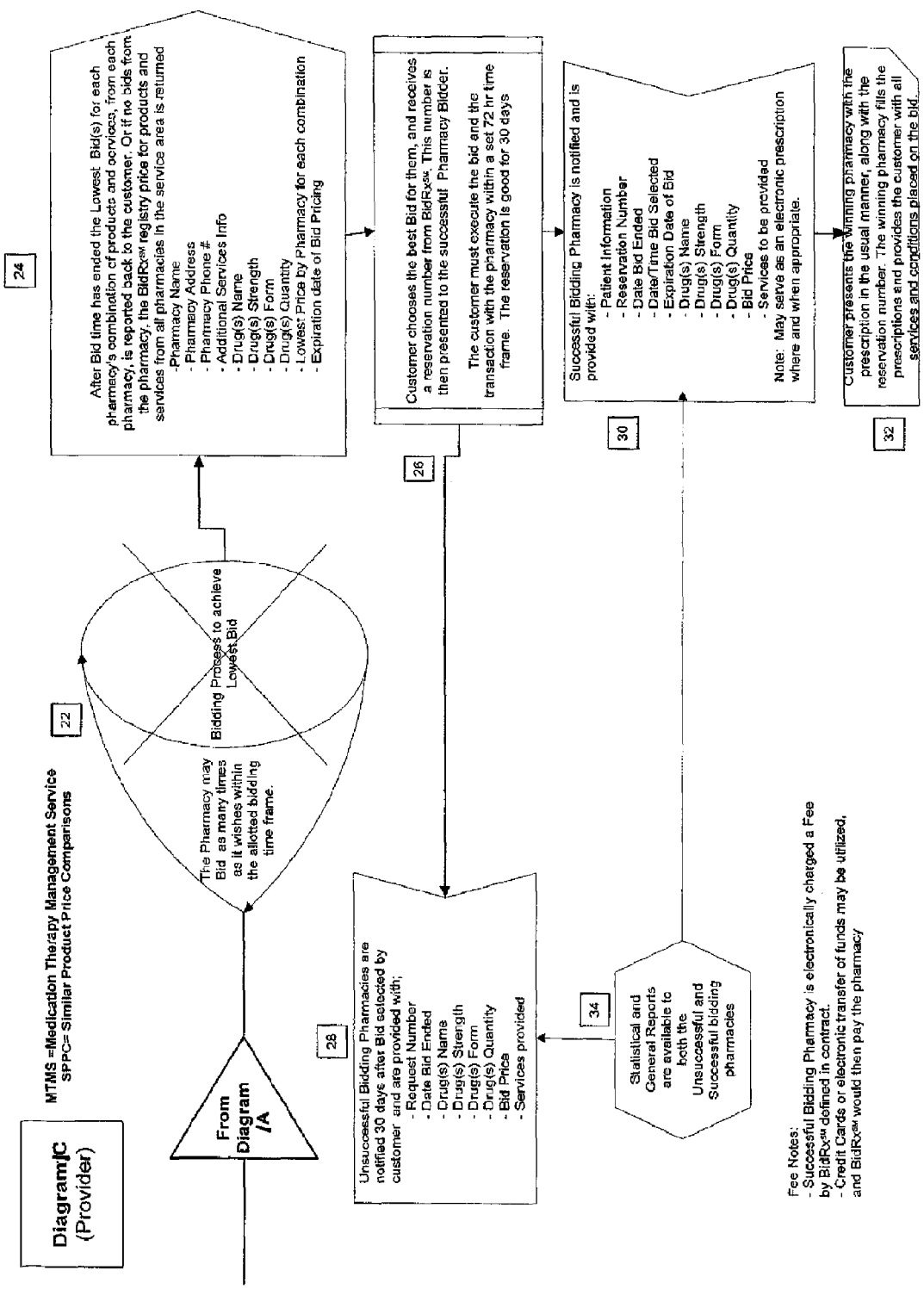
Figure 1D:
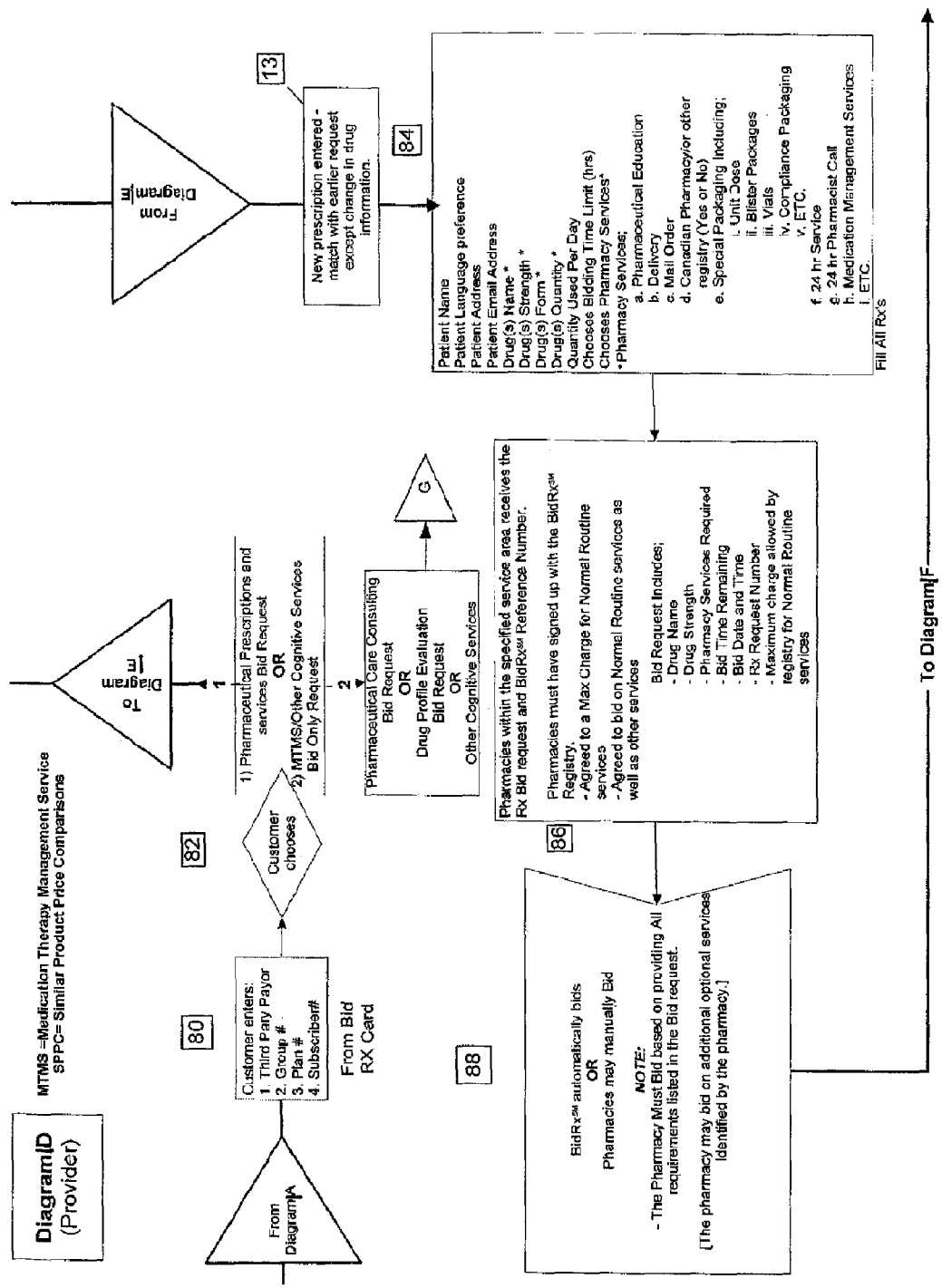

Referring to FIG. 1C, at Step 22 as bids from each of the responding pharmacies are received by the bidding service provider, they are posted for all responding pharmacies to see in a form of "reverse auction." The posting is preferably performed using an electronic network such as an intranet or the Internet, providing each responding pharmacy with real-time feedback regarding the status and relative placement of their respective bids. While the process is active, pharmacies that have been under-bid by a lower price offered by a competing pharmacy, may then manually submit new, lower bids and/or add services at no charge. In a preferred embodiment of the present invention, responding pharmacies are not permitted to raise their bid prices after they have been submitted.

For each drug or class of drug in the drug database, the pharmacy registrant is allowed to set a minimum price below the bidding service provider pharmacy registry price for products via a mathematical formula. Drugs may be listed as Not Available (NA). The registered pharmacy's minimum price will typically be based on standard industry price indices, e.g., either the Average Wholesale Price (AWP) or the Maximum Allowable Cost (MAC) within the commercially available drug database. (Example; PRICE=AWP−10% plus a $2.50 fee). In a further refinement of the invention, pharmacies may adjust the formula for each different third party payer in order to be included in more auctions. The pharmacy register price is the maximum allowable price that the pharmacies agree to in order to be included on the registry. Again the pharmacy register price will typically be based on a standard industry price index.

Drugs may be characterized by the Generic Product Identifier (GPI) code (a 14-character structure) or other drug classification systems. The 14 characters representing 7-two character pairs are used to define the various drug subsets. Drug Groups, Drug Classes, Drug Subclasses, Drug Names, Drug Dosage Form, and Drug Strength, are 6 of the subsets of partial GPIs found in the Medi-Span MDDB drug database (http://www.medi-span.com/). The GPI and other data elements such as the Generic Product Packaging Code (GPPC), and the National Drug Code (NDC) will be utilized to assist in pricing of drugs and to assist in determining Brand versus Generic drugs.

Once a pricing table or algorithm is completed by the registry pharmacy for each product the pharmacy wants to price differently then the standard BidRx$^{SM}$ registry price, the reverse auction begins with an automatic bidding module bidding for the pharmacy on each of the customers items in specified declining increments. The automatic bidding will continue as long as the pharmacy is not bidding against itself, or the minimum price is met. Minimum prices may be set by third party payers as a means to maintain marketplace competition.

A manual bidding process for the pharmacy providers would consist of a screen that allows a bidding pharmacy within the service area of the requests, to see all of the bidding service provider requests and current lowest bids. The pharmacy-determined price for services are placed in the pharmacy pricing and are added to the product bid for services requested. The screen would allow the pharmacy to manually enter in the price for each product and service. Use of the manual option also allows a pharmacy to bid by temporarily resetting its minimum for the auction or group of auctions and add services at no charge to try to obtain the best fit by the customer and win the bid.

For each service in the pharmacy service database the pharmacy is allowed to set a field in the database for a pharmacy-determined charge, No Charge (N/C), Not Available (N/A), and a minimum charge by amount or unit of service. Once the pricing table is set for services, the automatic bidding module will bid on each of the customers requested services with the pharmacy determined price, Services listed as (N/C) are added to each bid if the customer requested that service or not. Services that are offered with charges, but not requested by the customer are added to a viewable screen of services bid at Usual and Customary pricing for customers future reference.

When bidding starts at Step 12, the best bids from each of the responding pharmacies are reported back to the customer at Step 24. The customer is preferably notified electronically via an Email message or accessed over the Internet; however, alternate means such as telephone, facsimile and mail may also be used. Bid reporting at Step 40 may be provided to the customer continuously during the reverse auction and/or after the set bidding period closes.

The lowest bid for each combination of product and services from each pharmacy bidding is returned to the customer at Step 24. The pharmacy registry maximum prices for products and services are returned for all pharmacies in the service area that have no manual or automatic bid for a particular auction.

The customer interface at Step 26 allows the bid information to be displayed in several different ways such as:

1. Lowest to highest based on product price only
2. Lowest to highest based on combined product and service pricing
3. Lowest to highest based on combined products and services of pharmacy offering services beyond that requested.
4. Highest to lowest based on the number of services offered.
5. Others Note: The above lists contain all of the elements of the bid priced by item and totaled, as well as the Name, Address, Phone #, Fax #, and Email address of the pharmacy and pharmacy web site link if available.

At Step 26 the customer selects the best bid that matches the customer's individual needs, based on their individual preferences. Such preferences may include preferred pharmacies, prescription cost, ancillary services available and the proximity of the pharmacies to the customer. The customer may be given the option of selecting the winning bid prior to the close of the bidding period. The customer notifies the bidding service provider of their selection during this step, and the bidding service provider provides the customer with a reservation number and key code corresponding to the terms of the pharmacy's bid for the prescription.

At Step 28 unsuccessful responding pharmacies are notified with the bid number and, optionally, de-identified patient information. At Step 30, the successful responding pharmacy is also notified with the bid number, is provided with the same reservation number as the customer (as at Step 26) and may receive patient identified information. The successful and unsuccessful pharmacies are preferably notified via an Email message or via an Internet web site; however, alternate means such as telephone and facsimile may also be used. The prescription is filled by the successful responding pharmacy as at Step 32, in accordance with the terms of the pharmacy's winning bid of Step 26 and entering the key code, NDC number, and prescription number into the pharmacy's BidRx$^{SM}$ reservation. The key code acts as proof that the prescription was filled and, thereby, authorizes the bidding service provider to pay the pharmacy.

In Step 32 the customer then contacts the pharmacy by usual means and presents a valid prescription for the bid products along with the reservation number and key code. (This can only be done after a bid is awarded). The winning bid remains in the bidding service provider's system until the expiration date of the reservation. Only the customer and the winning pharmacy have access to the winning bid information, via login and password. The winning Pharmacy fills the prescription and provides the services specified in the reservation at the bid price.

In one embodiment, the prescription could be stored on the bidding system databases and transmitted electronically to the pharmacies (e-prescriptions). Such e-prescriptions could be sent by email intranet, Internet, Web or any other type of electronic transfer system where allowed or else by facsimile. Storing the prescription electronically on the bidding system allows the system to automatically generate, if refills are authorized, and transmit the refill for a copy of the prescription to a different pharmacy if the consumer switches pharmacies during a refill.

One advantage suitable to large scale pharmacies would be central fulfillment of prescription orders. For example, a chain of pharmacies in a large urban area, such as Manhattan, might want to store and process the drugs and other prescribed items outside of the urban area to reduce rental and real estate costs. The pharmacy could centrally fill the prescriptions at a remote location (e.g., outside the urban area)

and use the pick-up or delivery time specified by the consumer to provide just-in-time delivery of the filled prescriptions to other pharmacies.

After the reservation expires, the winning bid information is available, as shown in Step 34 on the bidding service provider's system to all pharmacies within the service area, minus the customer and pharmacy information. Pharmacies viewing this data should be able to perform queries on this information to allow them to improve their chances of winning new bids. Some examples are:
1. The number of successful bids per specified period.
2. The number of bids available per specified period
3. Percentage of successful bids by pharmacy in the specified period.
4. Winning bid prices for products and services over a time period (also available to customer).
5. List highest to lowest based upon a selection of the following;
   a. Product pricing database
   b. Services database Pharmacies receive the bid information and can:
1. Bid manually through the BidRx$^{SM}$ system user interface,
2. Let the BidRx$^{SM}$ system automatically bid the registry price for them,
3. Let the BidRx$^{SM}$ automatic bidding module bid down the price to a pharmacy set minimum.

Referring back to FIG. 1A, if the customer selects 2) at Step 10, (Medication Therapy Management/Other Cognitive Services Service Only Bid Request) they are asked to select from the following types of pharmaceutical cognitive services at Step 36:
1. Pharmaceutical Care Consulting and evaluation bid request
2. Drug Profile Evaluation bid request
3. Other Cognitive Services Typically, bidding service provider does not provide the services above but instead provides a system for customers to request bids for these services and third party providers of these services to bid, thereby resulting in a reservation for the services at the winning bid price. In an alternative embodiment, the bidding service provider may also be bid, under appropriate circumstances, to provide MTMS or other cognitive services. In a further alternative embodiment, the bidding service provider may, automatically or optionally for a fee, conduct MTMS/Other Cognitive Services based on the customer's record of prescriptions obtained by using the bidding system.

One form of MTMS/Other Cognitive Services is a Drug Profile Evaluation bid request (DPE). A DPE is a review of the customer's current drugs they are taking along with their diagnoses, allergies, age, sex, diet, lifestyle, etc. The review maximizes the effectiveness of the customers medications and minimizes cost. The following are some examples of items accomplished in this type of a review;
1. Drug use without indication—The customer is taking a medication for no medically valid indication.
2. Untreated indication—The customer has a medical problem that requires drug therapy but is not receiving a drug for that indication.
3. Improper drug selection—The customer has a drug indication but is taking the wrong drug, or is taking a drug that is not the most appropriate for the special needs of the customer.
4. Sub-therapeutic dosage—The customer has a medical problem that is being treated with too little of the correct medication.
5. Over dosage—The customer has a medical problem that is being treated with too much of the correct medication.
6. Adverse drug reaction—The customer has a medical problem that is the result of an adverse drug reaction or adverse effect.
7. Drug interaction—The customer has a medical problem that is the result of a drug-drug, drug-food, or drug-laboratory test interaction.
8. Medication monitoring—Evaluation bid request of medications for effectiveness and toxicity or adverse effects.
9. Medication costs—Intervention is needed to assist the customer with obtaining access to a lower cost medication or overcoming a barrier to medication access, such as a formulary restriction or prior authorization.

Another form of MTMS/Other Cognitive Services is Pharmaceutical Care. Pharmaceutical Care as outlined by the American Pharmacists Association (http://www.aphanet.org/) is a patient-centered, outcomes oriented pharmacy practice that requires the pharmacist to work in concert with the patient and the patient's other health care providers to promote health, to prevent disease, and to assess, monitor, initiate, and modify medication use to assure that drug therapy regimens are safe and effective. The goal of Pharmaceutical Care is to optimize the patient's health-related quality of life, and achieve positive clinical outcomes, within realistic economic expenditures. To achieve this goal, the following must be accomplished: (A) a professional relationship must be established and maintained; (B) patient-specific medical information must be collected, organized, recorded, and maintained; and, (C) patient-specific medical information must be evaluated and a drug therapy plan developed mutually with the patient.

The plan may have various components, which address each of the patient's diseases or conditions. In designing the plan, the MTMS provider must carefully consider the psychosocial aspects of the disease as well as the potential relationship between the cost and/or complexity of therapy and patient adherence. As one of the patient's advocates, the MTMS provider assures the coordination of drug therapy with the patient's other pharmacy providers and the patient. In addition, the patient must be apprised of (1) various pros and cons (i.e., cost, side effects, different monitoring aspects, etc.) of the options relative to drug therapy and (2) instances where one option may be more beneficial based on the MTMS provider's professional judgment. The essential elements of the plan, including the patient's responsibilities, must be carefully and completely explained to the patient. Information should be provided to the patient at a level the patient will understand. The drug therapy plan must be documented in the patient's pharmacy record and communicated to the patient's other healthcare providers as necessary.

Other cognitive service bids and service may be offered.

Figure 1E:
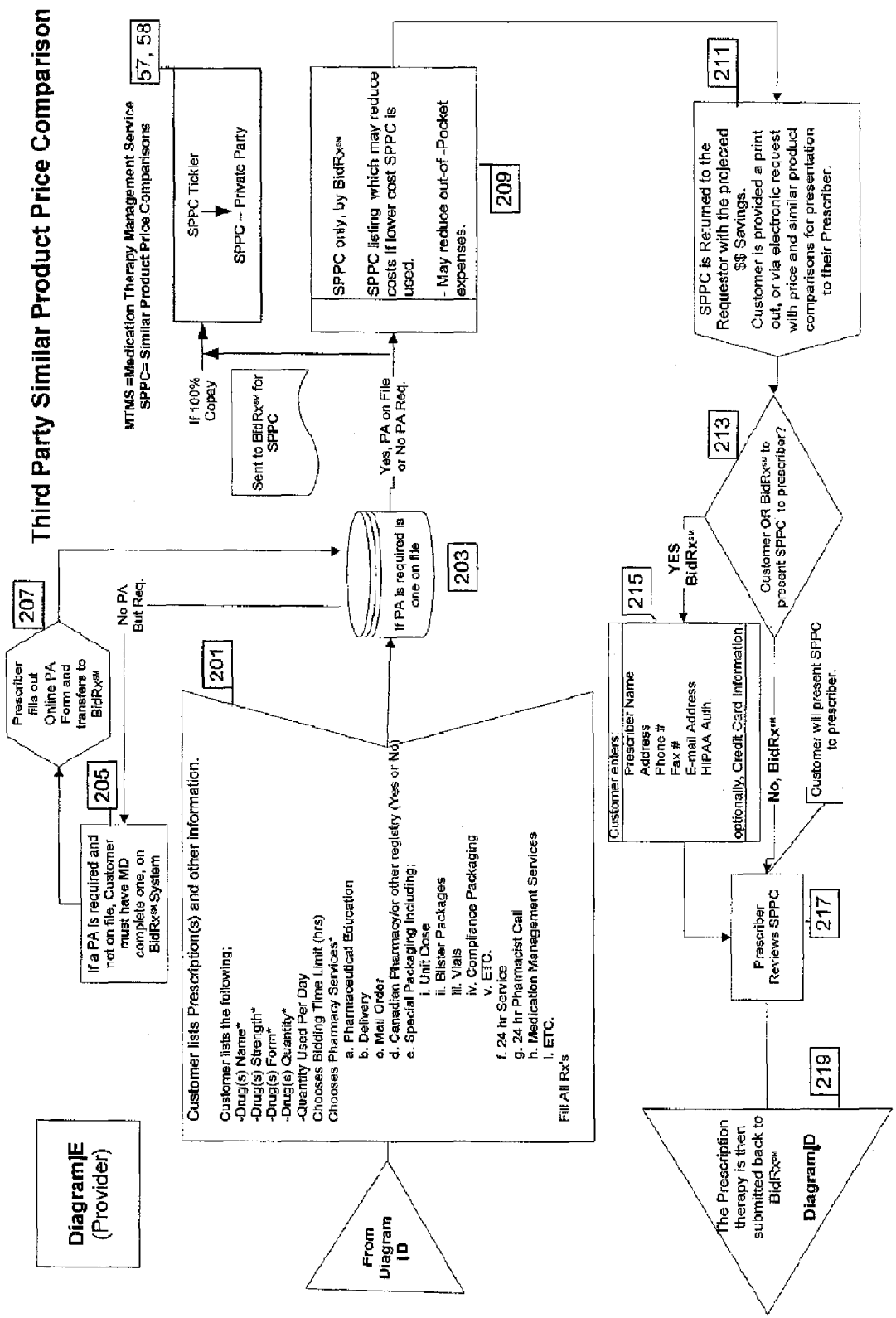
Figure 1F:
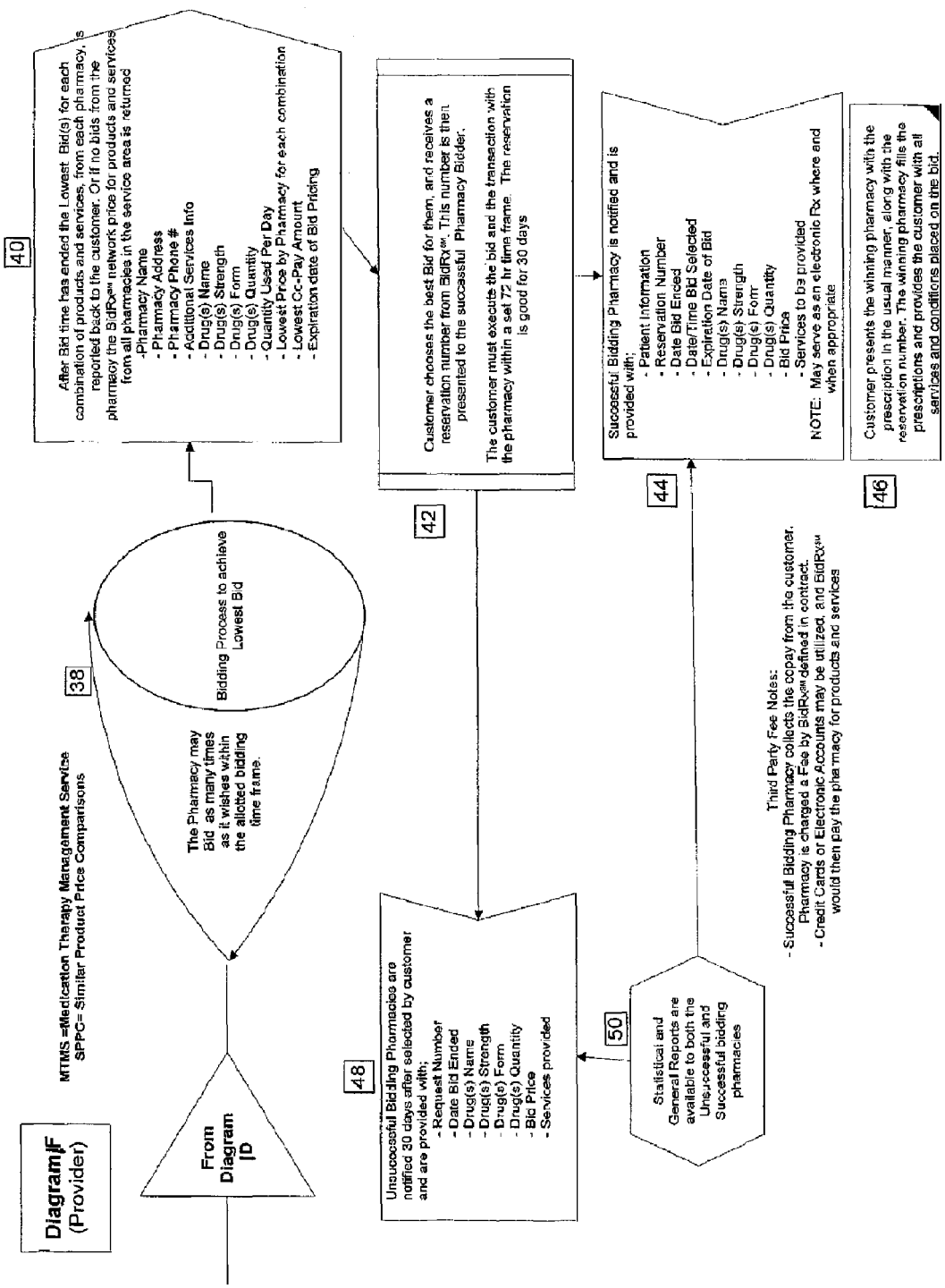
Figure 1G:
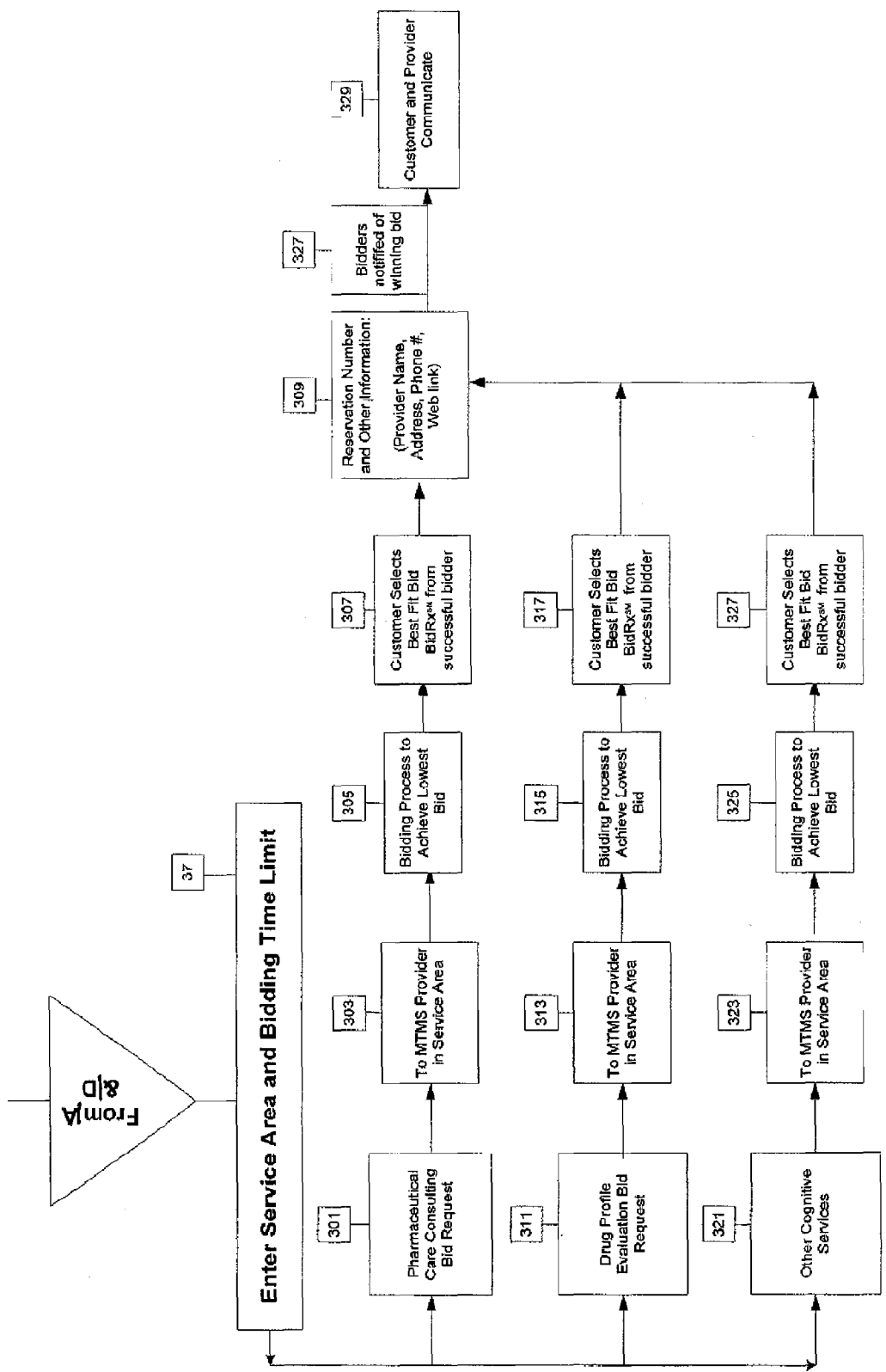

As shown in FIG. 1G, at Step 37, the customer is then requested to enter in the desired service area and desired bidding time limit. Different flow paths are then followed depending upon the choice at Step 36. A Pharmaceutical Care Consulting bid request 301, or a Drug Profile Evaluation bid request 311, or an Other Cognitive Services bid request 221 is submitted to the registry of MTMS/Other Cognitive Services Providers (Steps 303, 313, or 323, respectively) in the service area. The MTMS/Other Cognitive Services Providers in the different registries may be the same or different depending on the qualifications and interests of the individual MTMS Providers. Typically, MTMS service providers include, inter alia, pharmacists, physicians, nurses, prescribers, consultants, or other health professionals. The MTMS/Other Cognitive Services Providers (Steps 303, 313, 323) bid automatically and/ or manually in a reverse auction (Steps 305, 315, 325). The lowest bids from reverse auction (Steps 305, 315, 325) are reported to the customer either continuously during the auction and/or after the bidding period closes. The customer reviews the bids and selects the bid that best matches the customer's preferences (Steps 307, 317, or 327, respectively). The successful bidder and customer receive a reservation number and the customer also receives a key code that describes the conditions of the bid and price at Step 309. The customer additionally receives a key code that is used to verify the auction with the successful bidder. The customer can contact the successful bidder and provide to them the appropriate information for the review at Step 329. The successful bidder is typically charged a fee by the bidding service for facilitating the MTMS/Other Cognitive Services engagement.

The MTMS/Other Cognitive Services reservation number statement may contain instructions such as:

"If you want to execute your reservation, give this reservation number and key code along with a complete listing of all medications you currently take, including over-the-counter medications, vitamins, supplements and/or herbal remedies, to the MTMS/Other Cognitive Services Provider. The MTMS/Other Cognitive Services Provider can then review your prescription properly and provide to you the correct services. Other cognitive services, bids and services may be offered."

An advantage of this invention is that a continuous history of prescriptions obtained by the patient using the bidding system can be maintained even if the patient switches jobs, medical plans, physicians, hospitals, or insurance companies or pays for it out-of-pocket. Currently, the patient's prescription history is not frequently forwarded through such transitions and must be reconstructed after each change. Such reconstruction can lead to errors or omissions in the patient's history. With this system, the customer can obtain a report of all health related transactions, which the customer conducted through the bidding service provider, and provide that report to the winning MTMS/Other Cognitive Services Provider or any patient advocate.

Referring back to FIG. 1A and FIG. 1D, if the customer says "YES" to "Do you have a drug card that pays all or part of your pharmacy prescriptions?" at Step 8 they are asked to enter identification information (e.g., the following information (as it appears in customer's profile on the BidRx$^{SM}$ or member card or insurance card)) at Step 80;
 1. Whom is the prescription drug plan administered by*
 2. The Group Number*
 3. The Plan Number*
 4. Subscriber/Cardholder/Member Number*
  *This data comes from the third party client database matched with the bidding system, member card, and each plan is connected to eligibility, incentive, co-pay, and prior authorization databases.

After registering the customer may request a bid on Pharmaceutical Prescriptions and Services Bid Request. The customer will have a choice at Step 82 of whether to select; 1) Pharmaceutical Prescriptions and Services Bid Request or 2) Medication Therapy Management Service Only Bid Request.

If the customer selects 1) at Step 82, they will automatically have a SPPC as shown in FIG. 1E. If the drug is 100% co-pay the customer will be given an opportunity for a SPPC as described at Step 57. If SPPC is elected for a 100% co-pay medication, then the method goes to Step 58 unless no charge. If the customer selects 2) at Step 82, the process then proceeds to FIG. 1G as described before.

If a different product is selected from the SPPC, at Step 201 the customer enters the required information along with the new product selected in the SPPC, for example: Pharmaceutical Prescription; Customer Name; Customer Language preference; Customer Address and Customer Email Address; Drug(s) Name*; Drug(s) Strength*; Drug(s) Form*; Drug(s) Quantity*; Fill all prescriptions (if selected additional Prescription's are added at this time); pharmaceutical services*; Pharmaceutical Education; Delivery; Mail Order; Canadian Pharmacy (Yes or No); Special Packaging Including; Unit Dose, Blister Packages, Vials, Compliance Packaging, Etc.; 24 hr Service; 24 hr Pharmacist Call; Medication Management Services, Etc.; Chooses Bidding Time Limit (hrs).
 *=Items chosen from a database/List by pop-up box or other method.

If the third party program requires Prior Authorization for specific products or product groups, the following will happen;
 1. The bidding service provider system would allow these products to be entered, by an authorized "third party" representative into their own unique listing. Along with each specific product or group of products is a corresponding "Prior Authorization", (PA) form. The form may be available online for prescribers to fill out and submit back to the system.
 2. At Step 203 the bidding service provider system checks the products entered by the customer for "PA" requirements identified third parties listing.
 3. If the product is found in the "PA" listing, the customer is messaged back at Step 205 that their prescriber is required to enter information electronically into the bidding service provider system on the "Prior Authorization", (PA) form. The "PA" form will be easy to fill out by the prescriber at Step 207 with Yes/No answers or pop-up boxes.
 4. When the "Prior Authorization", (PA) form is completed and approved the bidding on the product(s) is allowed (Step 203).

The customer may be required by the third party payer to have a Similar Product Price Comparison (SPPC) or advocate or proxy prior to submitting their bid for product and services for bid (Step 209).

After the customer is provided at Step 211 with the results of the Similar Product Price Comparison (SPPC) the customer is then asked at Step 213 if they would like the bidding service provider to send the list to their prescriber. If "YES," then the bidding service provider proceeds to the pharmacy bidding review. If "YES," then the system asks at Step 215 for;
 1. Prescriber Name
 2. Address
 3. Phone Number
 4. Fax Number
 5. Email address if available
 6. HIPAA Authorization (Statement Check Box)
 7. Optionally, for the customer's credit card or other payment information if the third party does not pay for the bidding service provider to forward the SPPC results directly.

The prescriber reviews the SPPC list at Step 217, whether presented by the customer or the bidding service provider. The prescription, reflecting the prescriber's approval/disapproval of the SPPC listed options, is then resubmitted at Step 219 to the bidding system prior to Step 84 in FIG. 1D. At Step 84, all necessary prescription information is entered with the bidding service provider.

Pharmacies receive the bid information at Step 86 and can, at Step 88
 1. Bid manually through the bidding service provider system user interface,
 2. Let the bidding service provider system automatically bid the registry price for them, 3. Let the bidding service provider automatic bidding module bid down the price to a pharmacy set minimum.

The process continues at Step 38 as shown in FIG. 1F. At Step 38 as bids from each of the responding pharmacies are received by the bidding service provider, they are posted for all responding pharmacies to see in a form of "reverse auction." The reverse auction of Step 38 is the same as described earlier. The posting is preferably performed using an electronic network such as an intranet or the Internet, providing each responding pharmacy with real-time feedback regarding the status and relative placement of their respective bids. While the process is active, pharmacies that have been underbid by a lower price offered by a competing pharmacy, may then manually submit new, lower bids and/or add services at no charge. In a preferred embodiment of the present invention, responding pharmacies are not permitted to raise their bid prices after they have been submitted. The registry pharmacies can set minimum prices for the reverse auction as described earlier and/or bid manually. Otherwise, the registry pharmacies automatically submit the default bid which is the maximum price allowed for members of the registry.

When bidding starts at Step 38, the best bids from each of the responding pharmacies are reported back to the customer at Step 40. The customer is preferably notified electronically via an Email message or accessed over the Internet; however, alternate means such as telephone, facsimile and mail may also be used. Bid reporting at Step 40 may be provided to the customer continuously during the reverse auction and/or after the set bidding period closes.

The customer interface at Step 40 allows the bid information to be displayed in several different ways such as:
1. Lowest to highest based on product price only
2. Lowest to highest based on combined product and service pricing
3. Lowest to highest based on combined products and services of pharmacy offering services beyond that requested.
4. Highest to lowest based on the number of services offered.
5. Others Note: The above lists contain all of the elements of the bid priced by item and totaled, as well as the Name, Address, Phone #, Fax #, and email address of the Pharmacy and Pharmacy web site link if available.

At Step 42 the customer selects the best bid that matches the customer's individual needs, based on their individual preferences. Such preferences may include preferred pharmacies, prescription cost, ancillary services available and the proximity of the pharmacies to the customer. The customer may be given the option of selecting the winning bid prior to the close of the bidding period. The customer notifies the bidding service provider of the selection during this step, and the bidding service provider provides the customer with a reservation number and key code corresponding to the terms of the pharmacy's bid for the prescription.

At Step 44 unsuccessful responding pharmacies are notified. The successful responding pharmacy is also notified and provided with the same reservation number as the customer, as at Step 44. The successful and unsuccessful pharmacies are preferably notified via an Email message or via an Internet web site; however, alternate means such as telephone and facsimile may also be used. The prescription is filled by the successful responding pharmacy at Step 46, in accordance with the terms of the pharmacy's winning bid of Step 42 and entering the key code into the pharmacies BidRx$^{SM}$ reservation. The key code acts as proof that the prescription was filled and, thereby, authorizes the bidding service provider to pay the pharmacy.

In Step 46 the customer then contacts the pharmacy by usual means and presents a valid prescription for the bid products along with the reservation number and key code. (This can only be done after a bid is awarded). The winning bid remains in the bidding service provider's system until the expiration date of the reservation. Only the customer and the winning pharmacy have access to the winning bid information, via login and password. The winning pharmacy fills the prescription and provides the services specified in the reservation at the bid price.

After the reservation expires or the prescription is filled, the winning bid information is available, as shown in Step 48 on the bidding service provider's system to all pharmacies within the service area, minus the customer and pharmacy information. Pharmacies viewing this data should be able to perform queries 50 on this information to allow them to improve their chances of winning new bids. Some example queries are:
1. The number of successful bids per specified period.
2. The number of bids available per specified period
3. Percentage of successful bids by pharmacy in the specified period.
4. Winning bid prices for products and services over a time period (also available to customer).
5. List highest to lowest based upon a selection of the following;
   a. Product pricing database
   b. Services database It should be noted that the present invention may be used without limitation by customers who are participating in a healthcare insurance plan. Likewise, uninsured customers may use the present invention to obtain drug price discounts and increase the availability of desired pharmacy services while holding down the total cost of care.

Data mining may be conducted upon the information contained within the bidding system in order to generate a number of reports. As a general rule, whatever information an entity put into the system they can get back out as a report. A number of reports will be viewable online such as the SPPC list, ongoing auctions (by customers/proxy or pharmacy), summary reports of completed auctions, local area prices, list of all local pharmacies (which may also include links to the web pages of those pharmacies) and lists of services provided by those pharmacies. Likewise, prescribers may have access to reports on what they have done as a patient's proxy, PA approvals, and/or local area drug prices. Additional reports for pharmacies may include prices for auctions they have won, how many prescriptions they need to fill, comparisons of the actual sale price versus the bid cost, sales details for all pharmacies in the area (for sales that have been completed and given lag time such as 30 days), a projection of inventory needs based on the won auctions in the pharmacies queue, and a report on the maximum and minimum prices of all third party payers. Pharmacies may also get reports on individual pharmacies or regional pharmacies on a total corporate level. Customers can get reports on all of their bid prescription transactions. PhRMA may get reports on the de-identified customer data, details on what drugs are being purchased, etc.

Example

FIG. 2 is a timeline of a preferred embodiment of the invention showing the sequencing and interaction of the steps of the bidding process to provide drugs. A customer 101 registers 103 with a bidding system (BidRx$^{SM}$) 99. Preferably, such registration is online. The customer is then provided with a sign-on identifier 105. Alternatively, a prescriber or anyone else if consumer allows 107 can act as a proxy 109 for customer 101. Prescriber 107 may also register 111 as a prescriber and obtain a sign-on identifier 113.

Prequalified MTMS providers 115 register 117, either by paper or, where appropriate, online, and receive a sign-on identifier 119. Providers/pharmacies 121 register, either by paper, or where appropriate, online, and receive a sign-on identifier 125. The pharmacies provide a table 127, of minimum pricing and services offered, to bidding system 99. Bidding system 99 interacts with table 127 to set agreed starting bids and can also interact with the pharmacies 121 to inform them of maximum and minimum bids imposed by different third party payers 129.

Third party payers 129 register with bidding system 99, either by paper, or where appropriate, online and receive a sign-on identifier 133 entry of COB requirements. The third party payers submit a plan design 135 which includes co-pay, coordination of benefits, PA and other tables and minimum and maximum bids.

Pharmaceutical suppliers 137 (also known as PhRMA) register 139, either by paper or where appropriate, online, and receive a sign-on identifier 141. PhRMA 137 provides coupons/rebate tables 143 to bidding system 99.

An auction begins by the sign-on 145 of a customer or proxy. If the customer selects MTMS services 147 they are diverted to the appropriate modules. However, if the customer or proxy enters bid information 149 the bidding system 99 automatically checks third party eligibility 151 and if appropriate, third party prior approval requirements 153. If a third party prior approval check 153 is required, the PA request may be automatically sent to the prescriber and returned 155. If no prior authorization is required or if the prior authorization request is returned then in Step 157 the bid is submitted to the bidding system 99. At this point, the customer may request an SPPC comparison 159 or the customer's proxy may also request some SPPC 161. If the customer is eligible for third party payment, an SPPC request is automatically generated 165 with the associated fees typically charged to the third party payer 129. If the SPPC request is provided either by the customer 159 or the proxy 161, the customer enters payment information 163. At this point, if an SPPC request has been submitted through any of the prior means, an SPPC list 167 is generated and transmitted to the requestor 169. If the SPPC list is provided to the customer the customer has the choice of selecting one of the alternative medications from the list and/or submitting the SPPC list to the prescriber 169. Alternatively, if the third party payer or the prescriber requests the SPPC list, the SPPC list 167 may automatically be sent to the prescriber 107 to approve, deny and if necessary provide the prior authorization 169. At this point, the bid request is transmitted to the auction module 171. The auction 173 with automatic bidding 175 occurring nearly instantaneously with the beginning of the auction event. Customer 101 or the physician proxy 107 can review the bid status 175 and at any point select a bid 179 and thereby conclude the auction. While the auction 173 is occurring the pharmacy 121 may review ongoing auctions and manually bid on products and services in an attempt to win the right to fill this prescription 177. Unless previously terminated by the customer 101 or physician proxy 107, the auction 173 ends at Step 181 at the conclusion of the predetermined time limit. At Step 181 the customer either accepts one of the bids or denies all of them. If the customer accepts a bid, a reservation number and bid information (including a key code) 183 is transmitted to the customer. Simultaneously a reservation number (and information on the customer) 185 is transmitted to the winning pharmacy 121. Once the prescription has been filled and the pharmacy has been provided the key code couple to the customer's reservation pharmacy may provide NDC, prescription number, additional information, and electronic transfer of pharmacy fees 187 is sent from the winning pharmacy's account to the bidding system 99 account. Any coupons or rebates 189 from PhRMA 137 is then also transferred to the bidding system 99. Likewise, any third party fees 191 are electronically transferred to the bidding system 99. Subsequently, the third party payments and the PhRMA payments are transferred 193 to the pharmacy 121.

Another feature that can be added to the inventive system is providing for quality ratings. Providers and customers can be given the opportunity to provide feedback or quality ratings of each other based on the results of the transaction. Customers can then exclude providers that have poor quality ratings from the bidding process while providers can specify that they will not bid on any prescriptions for customers that have a poor quality rating. This system can also be used to aid a customer when choosing a provider or prescriber.

As described above, an invention is a complex system with many subsystems and optional features. While a preferred embodiment is to use the invention as an integral whole as described above, certain subsystems can be used alone or can be excluded from a system. For example, the system can be used without the reverse auction among the pharmacies. In this embodiment, all pharmacies within the registry agree to sell the prescribed product or service at the price set by the bidding service provider. The customer or proxy will then be given a list of pharmacies or providers that meet the geographical or other characteristics specified in the submitted bid. The customer or proxy can then choose the pharmacy or provider based on location, services, or any other idiosyncratic preference.

Another example would be excluding the participation of pharmacies in the process. The customer or proxy would be presented with the SPPC list of alternative medications or services with the prices as determined by coupons and third party benefits. Assuming the prescriber agrees and provides the suitable prescription, the customer can choose the best medication value for their situation. Once the customer and the prescriber agree on the product, the prescription can be filled at this price by the bidding service provider or designee.

The system embodiment of the invention requires a processing unit programmed with a rules engine capable of executing the desired steps of the process and of providing the desired functions as described herein. The processing unit must be in electronic communication with a database capable of storing the information input into the system as described herein. Such information includes, inter alia, the customer and prescription information, pricing rules, auction results, etc. The system is also in communication with input/output devices such as computer terminals, email devices and/or Internet access devices. Typically, the communication with the input/output devices is through one or more servers connected to an intranet, the Internet, or both.

From the above description of the invention, those skilled in the art will perceive improvements, changes, and modifications in the invention. Such improvements, changes, and modifications within the skill of the art are intended to be covered. Likewise, one skilled in the art will recognize that the order of certain steps in the method may be combined, deleted or rearranged without diminishing the scope of the invention.

What is claimed is:

1. A method for facilitating the delivery of prescription products or services, the method comprising the steps of:
providing, from a customer to a participating bidding service provider, prescription information and patient information relating to an unfilled prescription, wherein the unfilled prescription was provided to the customer by a prescriber;
electronically performing a similar product price comparison to identify a list of products or services potentially similar to the unfilled prescription along with relative costs for such identified similar products or services;
providing the customer with the results of the similar product price comparison;
communicating, from the customer to the processing unit, a select prescription comprising the unfilled prescription or a select similar product or service;
transferring information relating to the select prescription from the bidding service provider to a registry of pre-qualified prescription fulfillment providers;
conducting a reverse auction on a computer system in which the pre-qualified prescription fulfillment providers respond with interactive and iterative bids to fill the select prescription;
providing the customer with the details of the lowest bid of each responding prescription fulfillment provider that made at least one bid to fill the select prescription;
selecting the winning bid by the customer; and
providing the customer with a reservation, wherein the reservation comprises at least one coupon for an item other than the select prescription.

2. A method for facilitating the delivery of prescription products or services, the method comprising the steps of:
providing, from a customer to a participating bidding service provider, prescription information and patient information relating to an unfilled prescription, wherein the unfilled prescription was provided by a prescriber;
electronically performing a similar product price comparison to identify a list of products or services potentially similar to the unfilled prescription along with relative costs for such identified similar products or services;
providing the customer with the results of the similar product price comparison;
communicating, from the customer to the processing unit, a select prescription comprising the unfilled prescription or a select similar product or service;
transferring the information relating to the select prescription from the bidding service provider to a registry of pre-qualified prescription fulfillment providers;
conducting a reverse auction on a computer system in which the pre-qualified prescription fulfillment providers respond with interactive and iterative bids to fill the select prescription;
providing the customer with the details of the lowest bid of each responding prescription fulfillment provider that made at least one bid to fill the select prescription; and
selecting a bid of a prescription fulfillment provider by the customer, wherein the prescription fulfillment provider having the selected bid provides the select prescription from a central prefill location.

3. A method for facilitating the delivery of prescription products or services, the method comprising the steps of:
providing, from a customer to a participating bidding service provider, prescription information and patient information relating to an unfilled prescription, wherein the unfilled prescription was provided by a prescriber;
electronically performing a similar product price comparison to identify a list of products or services potentially similar to the unfilled prescription along with relative costs for such identified similar products or services;
providing the customer with the results of the similar product price comparison;
communicating, from the customer to the processing unit, a select prescription comprising the unfilled prescription or a select similar product or service;
transferring information relating to the select prescription from the bidding service provider to a registry of pre-qualified prescription fulfillment providers;
conducting a reverse auction on a computer system in which the pre-qualified prescription fulfillment providers respond with interactive and iterative bids to fill the select prescription;
providing the customer with the details of the lowest bid of each responding prescription fulfillment provider that made at least one bid to fill the select prescription; and
selecting the winning bid by the customer,
wherein the select prescription is sent electronically to the fulfillment provider having the winning bid.

4. A method for facilitating the delivery of prescription products or services, the method comprising the steps of:
providing, from a customer to a participating bidding service provider, prescription information and patient information relating to an unfilled prescription, wherein the unfilled prescription was provided by a prescriber;
electronically performing a similar product price comparison to identify a list of products or services potentially similar to the unfilled prescription along with relative costs for such identified similar products or services;
providing the customer with the results of the similar product price comparison;
communicating, from the customer to the processing unit, a select prescription comprising the unfilled prescription or a select similar product or service;
transferring information relating to the select prescription from the bidding service provider to a registry of pre-qualified prescription fulfillment providers;
conducting a reverse auction on a computer system in which the pre-qualified prescription fulfillment providers respond with interactive and iterative bids to fill the select prescription;
providing the customer with the details of the lowest bid of each responding prescription fulfillment provider that made at least one bid to fill the select prescription; and
selecting the winning bid by the customer,
wherein the fulfillment provider with the winning bid does not use the Internet to access the bidding service provider and reservation and transaction information is transmitted between the bidding service provider and the fulfillment provider with the winning bid through a data interchange system.

5. A method for facilitating the delivery of prescription products or services, the method comprising the steps of:
providing, from a customer to a participating bidding service provider, prescription information and patient information relating to an unfilled prescription, wherein the unfilled prescription was provided to the customer by a prescriber;
electronically performing a similar product price comparison to identify a list of products or services potentially similar to the unfilled prescription along with relative costs for such identified similar products or services;
providing the customer with the results of the similar product price comparison;

selecting a select prescription comprising the unfilled prescription or a select similar product or service, with the approval of the prescriber;

conducting a reverse auction on a computer system in which the pre-qualified prescription fulfillment providers respond with interactive and iterative bids to fill the select prescription;

providing the customer with the details of the lowest bid of each responding prescription fulfillment provider that made at least one bid to fill the select prescription;

providing the customer with a list of fulfillment providers based on criteria set by the customer;

selecting a fulfillment provider by the customer to fill the select prescription;

transferring prescription fulfillment information for the select prescription to the selected fulfillment provider; and providing the customer with a reservation, wherein the reservation comprises at least one coupon for an item other than the select prescription.

6. A method for facilitating the delivery of prescription products or services, the method comprising the steps of:

providing, from a customer to a participating bidding service provider, prescription information and patient information relating to an unfilled prescription, wherein the unfilled prescription was provided to the customer by a prescriber;

electronically performing a similar product price comparison to identify a list of products or services potentially similar to the unfilled prescription along with relative costs for such identified similar products or services;

providing the customer with the results of the similar product price comparison;

selecting a select prescription comprising the unfilled prescription or a select similar product or service, with the approval of the prescriber;

conducting a reverse auction on a computer system in which the pre-qualified prescription fulfillment providers respond with interactive and iterative bids to fill the select prescription;

providing the customer with the details of the lowest bid of each responding prescription fulfillment provider that made at least one bid to fill the select prescription;

providing the customer with a list of fulfillment providers based on criteria set by the customer;

selecting a fulfillment provider by the customer to fill the select prescription;

transferring prescription fulfillment information for the select prescription to the selected fulfillment provider; and providing the customer with a reservation, wherein the reservation comprises at least one coupon for an item other than the select prescription, wherein the pharmacy selected fulfillment provider provides the select prescription from a central prefill location.

\* \* \* \* \*